(12) United States Patent
Kawata et al.

(10) Patent No.: US 9,927,297 B2
(45) Date of Patent: Mar. 27, 2018

(54) OPTICAL MICROSCOPE AND SPECTROMETRY METHOD

(75) Inventors: Satoshi Kawata, Osaka (JP); Minoru Kobayashi, Osaka (JP); Taisuke Ota, Osaka (JP)

(73) Assignee: NANOPHOTON CORPORATION, Osaka (JP)

(*) Notice: Subject to any disclaimer, the term of this patent is extended or adjusted under 35 U.S.C. 154(b) by 31 days.

(21) Appl. No.: 14/004,645

(22) PCT Filed: Mar. 9, 2012

(86) PCT No.: PCT/JP2012/001664
§ 371 (c)(1),
(2), (4) Date: Sep. 11, 2013

(87) PCT Pub. No.: WO2012/124303
PCT Pub. Date: Sep. 20, 2012

(65) Prior Publication Data
US 2014/0002819 A1    Jan. 2, 2014

(30) Foreign Application Priority Data

Mar. 11, 2011 (JP) .................. 2011-054538

(51) Int. Cl.
*G01J 3/28* (2006.01)
*G01J 3/02* (2006.01)
(Continued)

(52) U.S. Cl.
CPC .......... *G01J 3/0205* (2013.01); *G01J 3/0208* (2013.01); *G01J 3/0229* (2013.01);
(Continued)

(58) Field of Classification Search
CPC ................ G02B 21/0064; G01J 3/0229; G01J 2003/045; G01J 2003/047; G01J 2003/1295
See application file for complete search history.

(56) References Cited

U.S. PATENT DOCUMENTS 1,964,365 A * 6/1934 Razek .................. G01J 3/0251
250/214 R
3,865,490 A * 2/1975 Grossman ................ G01J 3/02
356/301
(Continued)

FOREIGN PATENT DOCUMENTS

EP    1 431 795    6/2004
EP    2 249 194    11/2010
(Continued)

OTHER PUBLICATIONS

Supplementary European Search Report issued in corresponding EP application No. 12757318.6 dated Aug. 11, 2014.
(Continued)

*Primary Examiner* — Tri Ton
*Assistant Examiner* — Rufus Phillips
(74) *Attorney, Agent, or Firm* — Seyfarth Shaw LLP

(57) ABSTRACT

An optical microscope capable of performing measurement with a high resolution and a spectrometry method are provided. A spectrometry device according to an aspect of the present invention includes a Y-scanning unit that scans a spot position of the light beam on the sample, a beam splitter that separates, among the light beam incident on the sample, outgoing light, the outgoing light being emitted with a different wavelength, a spectroscope that spatially disperses the outgoing light separated by the beam splitter according to the wavelength, a detector that detects the outgoing light dispersed by the spectroscope, and a pinhole array 30 disposed on an incoming side of the spectroscope, (Continued)

a plurality of pinholes being arranged in the pinhole array, the plurality of pinholes being adapted to allow outgoing light to pass therethrough to the spectroscope side.

14 Claims, 14 Drawing Sheets

(51) Int. Cl.
  *G02B 21/00* (2006.01)
  *G01N 21/25* (2006.01)
  *G01N 21/65* (2006.01)
(52) U.S. Cl.
  CPC .......... *G01N 21/255* (2013.01); *G01N 21/65* (2013.01); *G02B 21/0064* (2013.01)

(56) References Cited

U.S. PATENT DOCUMENTS

| | | | | |
|---|---|---|---|---|
| 4,102,576 A * | 7/1978 | Maeda | ............... | G01J 3/12 356/333 |
| 5,283,624 A * | 2/1994 | Tsukada | ............... | G01J 3/04 356/319 |
| 5,321,501 A * | 6/1994 | Swanson | ............ | A61B 1/00096 250/227.27 |
| 5,434,671 A | 7/1995 | Sumiyoshi et al. | | |
| 5,489,980 A * | 2/1996 | Anthony | ............... | G01J 3/06 356/308 |
| 5,751,417 A * | 5/1998 | Uhl | ............... | 356/318 |
| 6,486,948 B1 * | 11/2002 | Zeng | ............... | G01J 3/04 356/301 |
| 7,034,270 B2 * | 4/2006 | Sasaki | ............... | G01N 21/6458 250/201.3 |
| 7,167,239 B2 * | 1/2007 | Yamamoto | ............... | G01J 3/28 356/326 |
| 7,502,108 B2 * | 3/2009 | Fritsch | ............... | G01B 11/306 356/326 |
| 7,961,398 B2 * | 6/2011 | Tocci | ............... | 359/629 |
| 8,773,760 B2 * | 7/2014 | Gmitro | ............... | G02B 21/0028 359/385 |
| 2002/0154319 A1 | 10/2002 | Yoshizawa et al. | | |
| 2007/0132994 A1 | 6/2007 | Kobayashi et al. | | |
| 2010/0188742 A1 | 7/2010 | Chen et al. | | |
| 2011/0299104 A1 * | 12/2011 | Seo | ............... | G01J 3/02 358/1.9 |

FOREIGN PATENT DOCUMENTS

| | | |
|---|---|---|
| JP | 63-309806 | 12/1988 |
| JP | 06-265318 | 9/1994 |
| JP | 11-118717 | 4/1999 |
| JP | 2002-267418 | 9/2002 |
| JP | 2007-121087 | 5/2007 |
| JP | 2007-179002 | 7/2007 |
| JP | 2010-054368 | 3/2010 |
| JP | 2010-256324 | 11/2010 |
| WO | WO 2009/029843 | 3/2009 |

OTHER PUBLICATIONS http://www.roper.co.jp/Htm/roper/tech_note/html/rp03.htm accessed Sep. 11, 2013.
Okuno, Masanari, et al.: "Multifocus Confocal Raman Microspecroscopy for Fast Multimode Vibartional Imaging of Living Cells," Optics Letters, vol. 35(4). pp. 4096-4098, 2010.
Japanese Office Action issued in Japanese Application No. 2011-054538 dated Feb. 24, 2015.

* cited by examiner

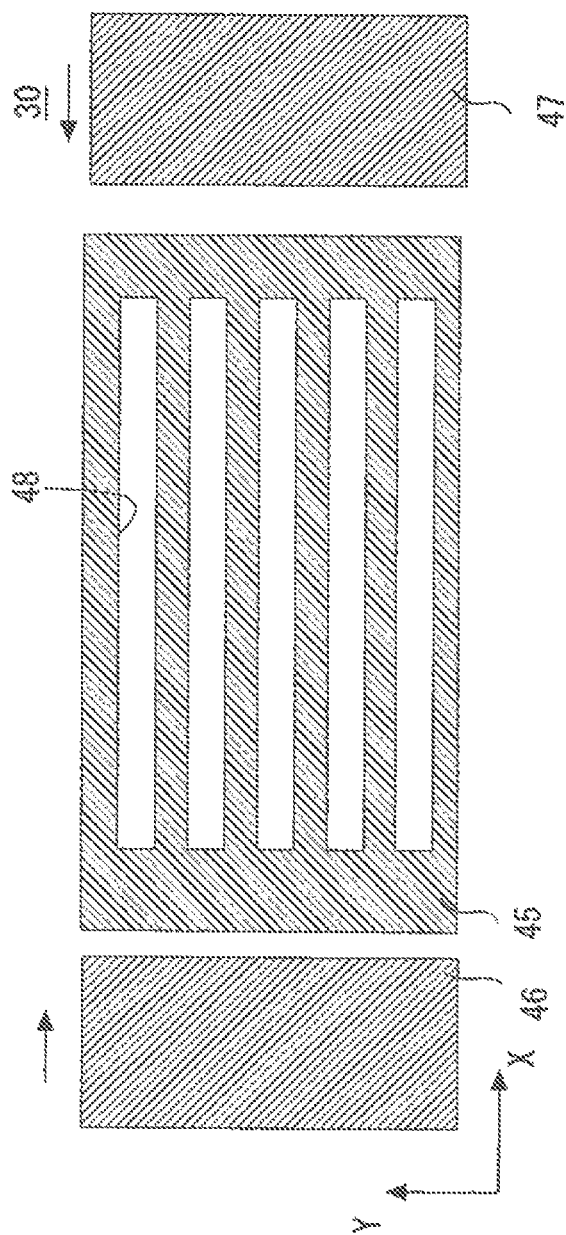

US 9,927,297 B2

OPTICAL MICROSCOPE AND SPECTROMETRY METHOD

This application is a U.S. National Stage Application of PCT international Patent Application No. PCT/JP2012/001664, which was filed on Mar. 9, 2012 and claims priority to Japanese Patent Application No. 2011-054538, which was filed Mar. 11, 2011, the disclosure of each of which is incorporated herein by reference in its entirety.

TECHNICAL FIELD

The present invention relates to an optical microscope and a spectrometry method, and in particular to an optical microscope and a spectrometry method in which light having a different wavelength from that of light applied to a sample is detected.

BACKGROUND ART

Raman spectrometry has an advantage that it can be performed regardless of whether the sample is a gas, a liquid, a crystal, or an amorphous solid, and regardless whether the temperature is high or low. Further, Raman spectrometry does not require any special measurement atmosphere such as a vacuum in the measurement. Further, Raman spectrometry has another advantage that it does not require any particular preprocessing of the sample and thus the sample can be measured as it is. Therefore, a number of measurements have been carried out by taking these advantages. By using Raman spectrometry, it is possible to observe molecules without dyeing them and to observe impurities in a semiconductor.

In order to perform such Raman spectrometry, Raman microscopes using spectroscopes have been disclosed (Patent literatures 1 and 2), in FIG. 1 of Patent literature 1, Raman-scattered light generated in a sample is divided into a spectrum by a spectroscope. Further, an entrance slit is disposed in front of the spectroscope. Then, Raman-scattered light generated in a certain point of the sample passes through a spot-like area of the entrance slit. An optical microscope disclosed in Patent literature 2 also includes an entrance slit. In an ideal case where no aberration occurs in the spectroscope, light that is generated in a certain point of the sample and passes through the spot-like area is dispersed in a $\lambda$-direction and detected in one pixel row of the detector. In such a case, Raman-scattered light having a specific wavelength generated in a certain point of the sample forms a light beam spot 81 on the light-receiving surface of the detector as shown in FIG. 13. FIG. 13 shows Raman-scattered light having two specific wavelengths.

However, when there is astigmatism in the optical system of the spectroscope, the spot elongates in the Y-direction. That is, the spot is widened in the direction perpendicular to the dispersing direction on the light-receiving surface. Therefore, as shown in FIG. 13, an elliptic spot(s) 82 is formed. Note that the spot 82 elongates in the longitudinal direction of the image of the entrance slit in the detector.

A technique for solving this astigmatism problem by correcting the aberration of the spectroscope has been disclosed (Non-patent literature 1). For example, in a spectroscope "SpectraPro series" from Acton Inc., a spectroscope in which a concave mirror has a toroidal surface rather than the spherical surface is used. In this way, the aberration can be corrected. Further, a spectroscope that corrects anastigmatic by using a plurality of concave mirrors has been disclosed (Patent literature 3).

Further, a multifocus confocal Raman microspecroscopy in which a fiber bundle is disposed in front of a spectroscope is disclosed (Non-patent literature 2). In this configuration, a light beam is converted into multi-beams by using a micro-lens array. Then, the multi-beams pass through a lattice-pattern pinhole array. Further, multi-beams emitted from the sample enter the fiber bundle through the lattice-pattern pinhole array. The emission ends of the fiber bundle are arranged in a row. Then, light emitted from the fiber bundle enters the spectroscope.

CITATION LIST

Patent Literature

Patent literature 1: Japanese Unexamined Patent Application Publication No. 2007-179002
Patent literature 2: Japanese Unexamined Patent Application Publication No. 2010-54368
Patent literature 3: Japanese Unexamined Patent Application Publication No. 2007-121087

Non Patent Literature

Non-patent literature 1: [Searched on Feb. 25, 2011], Internet http://www.roper.co.jp/Html/roper/tech_note/html/rp03.htm
Non-patent literature 2: Multifocus confocal Raman microspecroscopy for fast multimode vibrational imaging of living cells, Masanari Okuno and Hiro-o Hamaguchi, OPTICS LETTERS/Vol. 35, No. 24

SUMMARY OF INVENTION

Technical Problem

However, astigmatism cannot be sufficiently corrected even by these configurations. For example, in the case of a spectroscope having a focal length of 500 mm, the resolution deteriorates in the slit direction by the order of 100 µm.

The present invention has been made in view of the above-described problem, and an object thereof is to provide an optical microscope and a spectrometry method capable of performing measurement with a high resolution.

Solution to Problem

An optical microscope according to a first aspect of the present invention includes: a light source an objective lens that concentrates a light beam from the light source and applies the concentrated light beam onto a sample; scanning means for moving a position of the light beam relatively with respect to the sample and thereby scanning a spot position of the light beam on the sample; light branching means for separating, among the light beam incident on the sample, outgoing light emitted from the sample toward the objective lens side from the light beam emitted from the light source and incident on the sample, the outgoing light being emitted with a different wavelength; a spectroscope that spatially disperses the outgoing light separated by the light branch means according to a wavelength; a 2D (two-dimensional) array photodetector that includes light-receiving pixels arranged in an array and detects the outgoing light dispersed by the spectroscope; and light restricting means disposed on an incoming side of the spectroscope, a plurality of light-passage sections being arranged along a direction perpendicular to a dispersing direction of the spectroscope in the light restricting means, the plurality of light-passage sections being adapted to allow concentrated outgoing light to pass therethrough to the spectroscope side. With this configuration, it is possible to perform measurement with a high resolution in a short time.

An optical microscope according to a second aspect of the present invention is the above-described optical microscope, in which the plurality of light-passage sections are formed so that outgoing light that has passed through the plurality of light-passage sections does not overlap each other on a light-receiving surface of the 2D array photodetector. As a result, it is possible to reduce the effect of the astigmatism of the optical system of the spectroscope and thereby to improve the resolution.

An optical microscope according to a third aspect of the present invention is the above-described optical microscope, in which a size of the light-passage sections can he changed in a direction in parallel with the dispersing direction. As a result, it is possible to adjust the amount of light to be detected.

An optical microscope according to a fourth aspect of the present invention is the above-described optical microscope, in which the plurality of light-passage sections are formed by a pinhole array, pinholes being arranged in a row in the pinhole array. As a result, it is possible to limit the passage of light with a simple configuration.

An optical microscope according to a fifth aspect of the present invention is the above-described optical microscope, further including multi-beam forming means for forming a plurality of light beam spots incident on the sample so that measurement areas by the plurality of light-passage sections are simultaneously illuminated. As a result, it is possible to effectively use the light from the light source and thereby to perform measurement in a short time. Further, since no light is applied to the part that is not measured, the damage on the sample can be reduced.

An optical microscope according to a sixth aspect of the present invention is the above-described optical microscope, in which the multi-beam forming means arranges the plurality of light beam spots in a row. As a result, it is possible to use the light with efficiency.

An optical microscope according to a seventh aspect of the present invention is the above-described optical microscope, in which the scanning means includes: a first scanning unit that deflects the light beam from the light source in a first direction so that a position of the outgoing light in the light restricting means changes in an arrangement direction of the light-passage sections, the first scanning unit being disposed on an optical path extending from the light source to the light branching means and a second scanning unit that scans the spot position of the light beam on the sample in a second direction different from the first direction, the second scanning unit being disposed on an optical path extending from the light branching means to the sample. As a result, it is possible to reduce the measurement time.

An optical microscope according to an eighth aspect of the present invention is the above-described optical microscope, in which the scanning means further includes a third scanning unit that moves the position of the light beam relatively with respect to the sample and thereby scans the spot position of the light beam on the sample, and the measurement areas of the light-passage sections and the light beam spots are moved in the first direction on the sample by the scanning of the third scanning unit. As a result, it is possible to measure a desired area.

An optical microscope according to a ninth aspect of the present invention is the above-described optical microscope, further including light conversion means for converting the light beam from the light source into line-shaped light, in which the line-shaped light is incident on the sample, the line-shaped light extending along a direction corresponding to the arrangement direction of the light-passage sections. As a result, it is possible to eliminate the need for the scanning in the arrangement direction.

A spectrometry method according to a tenth aspect of the present invention includes: concentrating a light beam from a light source and applying the concentrated light beam onto a sample; moving a position of the light beam relatively with respect to the sample and thereby scanning a spot position of the light beam on the sample; separating, among the light beam incident on the sample, outgoing light emitted from the sample toward the objective lens side from the light beam emitted from the light source and incident on the sample, the outgoing light being emitted with a different wavelength; concentrating the outgoing light separated from the light beam; applying the concentrated outgoing light onto light restricting means, a plurality of light-passage sections being arranged in the light restricting means, the plurality of light-passage sections allowing the concentrated outgoing light to pass therethrough; dispersing the outgoing light that has passed through the light passage sections, in a direction perpendicular to an arrangement direction of the light-passage sections according to a wavelength; and detecting, by a 2D array photodetector including light-receiving pixels arranged in an array, the dispersed outgoing light. With this configuration, it is possible to perform measurement with a high resolution in a short time.

A spectrometry method according to an eleventh aspect of the present invention is the above-described spectrometry method, in which the plurality of light-passage sections are formed so that outgoing light that has passed through the plurality of light-passage sections does not overlap each other on a light-receiving surface of the 2D array photodetector. As a result, it is possible to reduce the effect of the astigmatism of the optical system of the spectroscope and thereby to improve the resolution.

A spectrometry method according to a twelfth aspect of the present invention is the above-described spectrometry method, in which a size of the light-passage sections can be changed in a direction in parallel with the dispersing direction. As a result, it is possible to adjust the amount of light to be detected.

A spectrometry method according to a thirteenth aspect of the present invention is the above-described spectrometry method, in which the plurality of light-passage sections are formed by a pinhole array, pinholes being arranged in a row in the pinhole array. As a result, it is possible to limit the passage of light with a simple configuration.

A spectrometry method according to a fourteenth aspect of the present invention is the above-described spectrometry method, in which a plurality of light beam spots incident on the sample are formed so that measurement areas by the plurality of light-passage sections are simultaneously illuminated. As a result, it is possible to effectively use the light from the light source and thereby to perform measurement in a short time. Further, since no light is applied to the part that is not measured, the damage on the sample can be reduced.

A spectrometry method according to a fifteenth aspect of the present invention is the above-described spectrometry method, in which the plurality of light beam spots on the sample are arranged in a row. As a result, it is possible to use the light with efficiency.

A spectrometry method according to a sixteenth aspect of the present invention is the above-described spectrometry method, in which the spot position of the light beam on the sample is scanned in a first direction so that a line-shaped area on the sample is measured, and after the measurement for the line-shaped area, the spot position of the light beam on the sample is scanned in a second direction. As a result, it is possible to reduce the measurement time.

A spectrometry method according to a seventeenth aspect of the present invention is the above-described spectrometry method, in which when the spot position of the light beam on the sample is scanned in the first direction, the light beam from the light source is deflected in the first direction without descanning the light beam, and then the measurement area of the light-passage sections on the sample is moved in the first direction. As a result, it is possible to measure a desired area.

A spectrometry method according to an eighteenth aspect of the present invention is the above-described spectrometry method, in which the light beam from the light source is converted into line-shaped light, and the line-shaped light is incident on the sample, the line-shaped light extending along a direction corresponding to the arrangement direction of the light-passage sections. As a result, it is possible to eliminate the need for the scanning in the arrangement direction.

Advantageous Effects of Invention

According to the present invention, it is possible to provide an optical microscope and a spectrometry method capable of performing measurement with a high resolution.

BRIEF DESCRIPTION OF DRAWINGS

FIG. 7A is a plane view showing a second configuration in which the size of pinholes can be changed;

DESCRIPTION OF EMBODIMENTS

First Exemplary Embodiment

Figure 1:
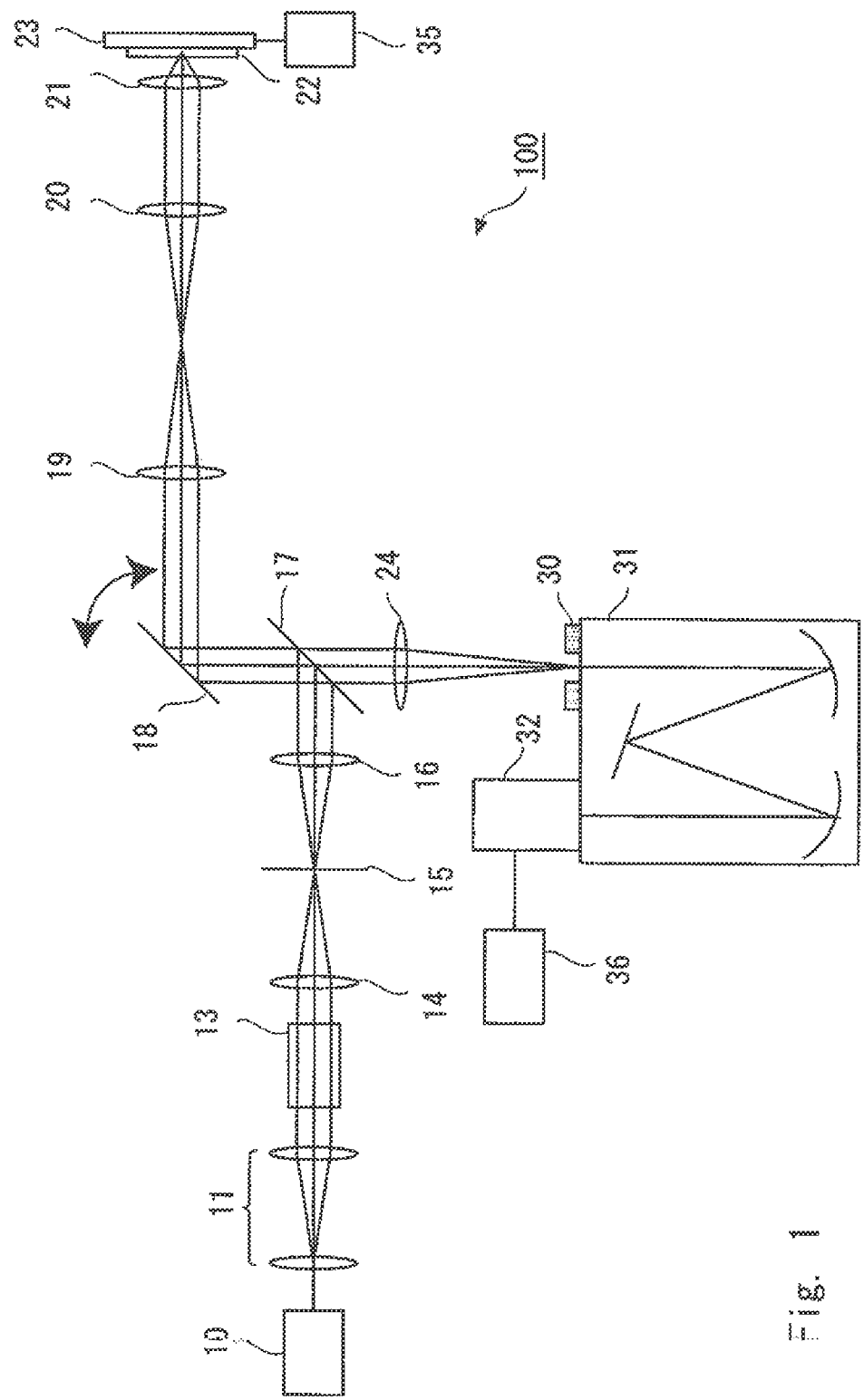
FIG. 1 shows a configuration of an optical microscope according to a first exemplary embodiment.

Exemplary embodiments to which the present invention can be applied are explained hereinafter. The following explanation is made only for explanatory purpose, and the present invention is not limited to the below-shown exemplary embodiments. For ease of explanation, the following description is given in an abbreviated and simplified manner as appropriate. Further, those skilled in the art will recognize that components can be readily changed, added, and/or replaced in the following exemplary embodiments within the scope of the invention. Note that the same components are denoted by identical reference numerals throughout the drawings, and description thereof is omitted if not necessary.

First Exemplary Embodiment of the Invention

An optical microscope according to an exemplary embodiment of the present invention is explained with reference to FIG. 1. FIG. 1 schematically shows a configuration of an optical system of an optical microscope according to this exemplary embodiment. An optical microscope 100 includes, as a configuration for observing a sample 22, a laser light source 10, a beam expander 11, a Y-scanning unit 13, a lens 14, a diaphragm 15, a lens 16, a beam splitter 17, an X-scanning mirror 18, a lens 19, a lens 20, an objective lens 21, a stage 23, a lens 24, a spectroscope 31, a detector 32, a stage driving unit 35, and a processing unit 36. The spectroscope 31 includes a pinhole array 30 on the incoming side.

The optical microscope 100 is a Raman microscope. The optical microscope 100 applies a light beam emitted from the laser light source 10 onto the sample 22 and detects Raman-scattered light from the sample 22 with the detector 32. Further, since the spectroscope 31 divides the Raman-scattered light into a spectrum, the optical microscope 100 can observe a Raman spectrum. Since the optical microscope 100 can perform scanning in the XY-directions (horizontal directions) and in the Z-direction (vertical direction), the optical microscope 100 can measure a 3D (three-dimensional) Raman spectrum image.

Firstly, the overall configuration of the optical microscope 100 is described with reference to FIG. 1. The laser light source 10 emits monochromatic laser light. There are no particular restrictions on the laser light source 10 to be used. However, it is preferable to use a light source having a narrow spectrum width in order to achieve a high spectral resolution. A light beam from the laser light source 10 is expanded by the beam expander 11 and then enters the Y-scanning unit 13. The Y-scanning unit 13 is, for example, an acousto-optic device or galvano mirror. The Y-scanning unit 13 changes the outgoing angle of the incident light beam and thereby deflects the light beam. As a result, the incident position of the light beam is changed along the Y-direction on the sample 22. That is, the Y-scanning unit 13 scans (i.e., moves) the light beam in the Y-direction. Note that the deflection angle at the Y-scanning unit 13 is controlled according to an electric signal from the processing unit 36. The light beam deflected at the Y-scanning unit 13 is refracted by the lens 14 and then enters the diaphragm 15. Note that the lens 14 concentrates the light beam on the surface of the diaphragm 15. The diaphragm 15 has, for example, a circular aperture and blocks the light beam incident on the outside of the aperture. That is, the diaphragm 15 restricts the passage of the light beam incident on the outside the aperture.

The light beam that has passed through the diaphragm 15 is refracted by the lens 16 and is incident on the beam splitter 17. The beam splitter 17 is, for example, a dichroic mirror and reflects light having a laser wavelength toward the sample 22. As the dichroic mirror, an "edge filter" available from Semrock Inc, can be used. The light reflected by the beam splitter 17 is incident on the X-scanning mirror 18. The X-scanning mirror 18 is, for example, a galvano mirror, and deflects the light beam by changing the angle of the reflection surface. That is, since the inclination angle of the reflection surface of the X-scanning mirror 18 can be changed with respect to the optical axis, the outgoing angle of the light beam can be changed. The incident position of the light beam on the sample 22 is changed along the X-direction. As a result, the light beam can be scanned (i.e., moved) in the X-direction. Note that the deflection angle of the light beam at the X-scanning mirror 18 is controlled according to an electric signal from the processing unit 36. Further, since the X-direction and the Y-direction are orthogonal to each other, the scanning can be performed in a 2D area on the sample 22 by performing the scanning in the XY-directions by using the X-scanning mirror 18 and the Y-scanning device 13.

The light beam scanned by the X-scanning mirror 18 is refracted by the lenses 19 and 20 and then enters the objective lens 21. The objective lens 21 concentrates the light beam and applies the concentrated beam onto the sample 22. That is, the objective lens 21 concentrates the light beam on the sample 22 and thereby illuminates the sample 22. As a result, a spot-like area is illuminated on the sample 22. As for the objective lens 21, Apochromat with NA 1.2×60 available from Nikon Corporation, for example, can be used.

The light incident on the sample 22 is partially Raman-scattered. Part of the incident light incident on the sample 22 that is emitted toward the objective lens 21 side by the Raman scattering is defined as "outgoing light". That is, part of the Raman-scattered light that enters the objective lens 21 is defined as "outgoing light". The Raman scattered outgoing light has a different wavelength from that of the incoming light. That is, the outgoing light is scattered while its frequency is shifted from the frequency of the incoming light due to the Raman shift. The spectrum of this outgoing light becomes the Raman spectrum. Therefore, by measuring the spectrum of the outgoing light, it is possible to determine the chemical structure and physical state of a substance(s) contained in the sample 22. That is, the Raman spectrum contains information about the vibration(s) of the material(s) constituting the sample 22. Therefore, by dispersing the outgoing light into a spectrum by using the spectroscope 31 and thereby detecting the spectrum of the outgoing light, it is possible to determine a substance(s) contained in the sample 22. Then, by scanning (i.e., moving) the focal point of the incident light in the XYZ-directions and thereby measuring the spectrum of the outgoing light emitted from the entire or part of the sample 22, it is possible to perform a 3D measurement of the Raman spectrum. By paying attention to a specific wavelength(s) in the measured Raman spectrum, it is also possible to measure the 3D spatial distribution of a specific substance(s). Specifically, when the sample 22 is a living cell, it is possible to measure the spatial distribution of nucleic acids or lipids in the cell, or the spatial distribution of sucrose or polystyrene spheres.

Note that the sample 22 is placed on the stage 23. The stage 23 is, for example, an XYZ-stage. This stage 23 is driven by the stage driving unit 35. By driving the stage 23 in the XY-directions by using the stage driving unit 35, it is possible to illuminate an arbitrary area of the sample 22. Further, by driving the stage in the Z-direction by using the stage driving unit 35, it is possible to change the distance between the objective lens 21 and the sample 22. Therefore, it is possible to change the focal point of the objective lens 21 along the optical axis direction. Since the optical microscope 100 according to the present invention constitutes a laser confocal microscope as described later, it is possible to perform scanning in the Z-direction by changing the focal point. That is, by moving the stage in the Z-direction, it is possible to take a tomographic image of the sample 22. It is possible to detect Raman-scattered light that is emitted from an arbitral height in the Z-direction of the sample 22 and thereby to measure a three-dimensional Raman spectrum image. The processing unit 36 supplies a control signal(s) to the stage driving unit 35 and thereby controls the driving of the stage 23.

The outgoing light that is Raman-scattered on the sample 22 placed on the stage 23 and then enters the objective lens 21 propagates through the same optical path as that of the incoming light. That is, the outgoing light is refracted by the objective lens 21, refracted by the lens 20 and the lens 19, and incident on the X-scanning mirror 18. The X-scanning mirror 18 reflects the outgoing light that is incident on the X-scanning mirror 18 toward the beam splitter 17. In this process, the outgoing light is descanned by the X-scanning mirror 18. That is, since the outgoing light is reflected on the X-scanning mirror 18, the outgoing light propagates in the opposite direction to the traveling direction of the incoming light that is emitted from the laser light source 10 and is incident on the X-scanning mirror 18. Further, Rayleigh-scattered light from the sample 22 also propagates through the same optical path as that of the Raman-scattered light.

The outgoing light reflected by the X-scanning mirror 18 is incident on the beam splitter 17. The beam splitter 17 is, for example, a dichroic mirror, and branches the outgoing light emitted from the sample 22 and the incoming light that is emitted from the laser light source 10 and is incident on the sample 22 based on the wavelength. That is, the beam splitter 17 is disposed in such a manner that its reflection plane is inclined with respect to the optical axis of the incoming light. Since the outgoing light from the sample 22 passes through the beam splitter 17, the optical axis of the outgoing light from the sample 22 is changed from the optical axis of the incoming light that is emitted from the laser light source 10 and is incident on the sample 22. Therefore, it is possible to separate the outgoing light emitted from the sample 22 from the incoming light that is emitted from the laser light source 10 and is incident on the sample 22.

Further, the beam splitter 17, which is a dichroic mirror, has such a characteristic that the beam splitter 17 reflects the light having the wavelength of the laser light source 10 and allows the Raman-scattered light to pass therethrough. Therefore, the Rayleigh-scattered light from the sample 22 having the wavelength of the laser light source 10 is reflected on the beam splitter 17, and the Raman-scattered light passes through the beam splitter 17. That is, by using a dichroic mirror as the beam splitter 17, it is possible to eliminate the Rayleigh-scattered light based on the wavelength difference between the Rayleigh-scattered light and the Raman-scattered light. Further, most of the laser light from the laser light source 10 is reflected on the beam splitter 17 and travels toward the sample 22. As a result, it is possible to reduce the loss of the laser light and thereby detect only the Raman-scattered light with efficiency. Note that the reflection property of the dichroic mirror may be determined according to the range of the spectrum to be measured. Note that the beam splitter 17 is disposed between the sample 22 and the Y-scanning device 13. Therefore, the beam splitter 17 separates the outgoing light that has not yet been descanned by the Y-scanning device 13 from the light beam emitted from the laser light source 10.

The outgoing light that has passed through the beam splitter 17 is refracted at the lens 24 and enters the pinhole array 30 disposed on the incoming side of the spectroscope 31. In this process, the lens 24 concentrates the outgoing light on the pinhole array 30. That is, the lens 24 forms an enlarged image of the illuminated area of the sample 22 on the pinhole array 30. A plurality of pinholes are formed in the pinhole array 30. These pinholes are arranged in a row along the direction corresponding to the Y-direction. That is the pinholes of the pinhole array 30 are arranged in the direction corresponding to the scanning direction (Y-direction) of the Y-scanning device 13 on the sample 22.

The lens 24 refracts the outgoing light and thereby forms an image on the pinhole array 30. Note that since the incoming light is formed into a spot-like image on a certain plane of the sample 22, the outgoing light is concentrated into a spot-shape on the pinhole array 30. The arrangement direction of the pinholes of the pinhole array 30 is conformed to the scanning direction of the Y-scanning device 13. The outgoing light is incident on the beam splitter 17 without being descanned by the Y-scanning device 13. Therefore, when scanning is performed by the Y-scanning device 13, the spot position of the light beam moves in the arrangement direction of the pinholes on the pinhole array 30. The components are arranged so that the light that has been scanned in the Y-direction on the sample 22 forms an image in the place where the pinholes of the pinhole array 30 are arranged. In other words, the pinhole array 30 and the sample 22 are disposed so that they have a mutually-conjugate relation.

Therefore, the Raman microscope is constructed as a confocal optical system. That is, the diaphragm 15 and the certain plane of the sample 22 are disposed so that they have a mutually-conjugate relation, and the certain plane of the sample 22 and the pinhole array 30 are disposed so that they have a mutually-conjugate relation. The incoming light is concentrated into a spot-shape on the XY-plane on which the diaphragm 15 is disposed and on the certain plane of the sample 22. Then, the outgoing light that has been scattered and emitted from the sample 22 is concentrated into a spot-shape on the pinhole array 30. The pinhole array 30 has pinholes arranged along the Y-direction, and allows only the outgoing light that enters the pinholes to pass therethrough toward the detector 32 side. By forming each of the illumination optical system from the laser light source 10 to the sample 22 and the observation optical system from the sample 22 to the detector 32 as an image-forming optical system as described above, it is possible to form a confocal Raman microscope. As a result, it is possible to carry out measurement in the Z-direction with a high resolution. Further, by moving the stage 23 in the Z-direction, it is possible to separate Raman-scattered light emitted from an arbitral height of the sample 22 from Raman-scattered light emitted from other heights and thereby detect the Raman-scattered light emitted from the arbitral height of the sample 22.

The outgoing light that has passed through the pinhole array 30 enters the main body of the spectroscope 31. The spectroscope 31 includes a spectral element such as a diffraction grating (grating) or a prism, and spatially disperses the outgoing light, which has entered through the pinhole array 30, according to its wavelength. In the case where the spectroscope 31 uses a reflective grating, the spectroscope 31 further includes an optical system including a concave mirror that guides the outgoing light from the pinhole array 30 to the spectral element and another concave mirror that guides the outgoing light that is divided into a spectrum by the spectral element to the detector 32. Needless to say, a spectroscope 31 having a configuration other than the above-shown configuration may be also used. The outgoing light is dispersed by the spectroscope 31 in the direction perpendicular to the arrangement direction of the pinhole array 30. That is, the spectroscope 31 wavelength-disperses the outgoing light in the direction perpendicular to the arrangement direction of the pinholes. The outgoing light that is divided into a spectrum by the spectroscope 31 enters the detector 32. The detector 32 is an area sensor in which light-sensitive elements are arranged in a matrix. Specifically, the detector 32 is a 2D array photodetector such as a 2D CCD camera in which pixels are arranged in an array.

For example, a cooled CCD can be used for the detector 32. Specifically, a 1340×400 pixel electronic cooled CCD (cooling temperature −80° C.) available from Princeton instrument can be used as the detector 32. Further, the detector 32 can be equipped with an image intensifier. The pixels of the detector 32 are arranged along the direction corresponding to the pinhole array 30. Therefore, one of the arrangement directions of the pixels of the detector 32 conforms to the arrangement direction of the pinholes and the other arrangement direction conforms to the dispersion direction of the spectroscope 31. The direction corresponding to the arrangement direction of the pinholes of the detector 32 is defined as "Y-direction" and the direction perpendicular to the arrangement direction, i.e., the direction along which the outgoing light is dispersed by the spectroscope 31 is defined as "X-direction".

The detector 32 outputs detection signals each representing the light intensity of the outgoing light received at each pixel to the processing unit 36. The processing unit 36 is for example, an information processing apparatus such as a personal computer (PC), and stores the detection signals supplied from the detector 32 into a memory or the like. Then, the processing unit 36 performs predetermined processing on the detection result and displays the processed result on a monitor. Further, the processing unit 36 controls the scanning performed by the Y-scanning device 13 and the X-scanning mirror 18, and controls the driving of the stage 23. Note that the X-direction of the detector 32 corresponds to the wavelength (frequency) of the outgoing light. That is, in a row of pixels arranged in the X-direction, pixels located at one end detect outgoing light having a long wavelength (low frequency) and pixels located at the other end detect outgoing light having a short wavelength (high frequency). Therefore, the distribution of light intensities in the X-direction of the detector 32 represents the distribution of a Raman spectrum.

By scanning the laser light in the Y-direction by using the Y-scanning unit 13, it is possible to illuminate a line-shaped area. Further, the scanning cycle of the Y-scanning unit 13 is made sufficiently shorter than one frame of the detector 32. As a result, it is possible to measure outgoing light beams from a plurality of spots on the sample 22 at a time. The outgoing light beams from a plurality of spots on the sample 22 are detected in one frame. Therefore, it is possible to reduce the measurement time, Further, the objective lens 21 concentrates the laser light so that the laser light forms a point-like spot on the sample 22. As a result, it is possible to improve the spatial resolution.

Figure 2:
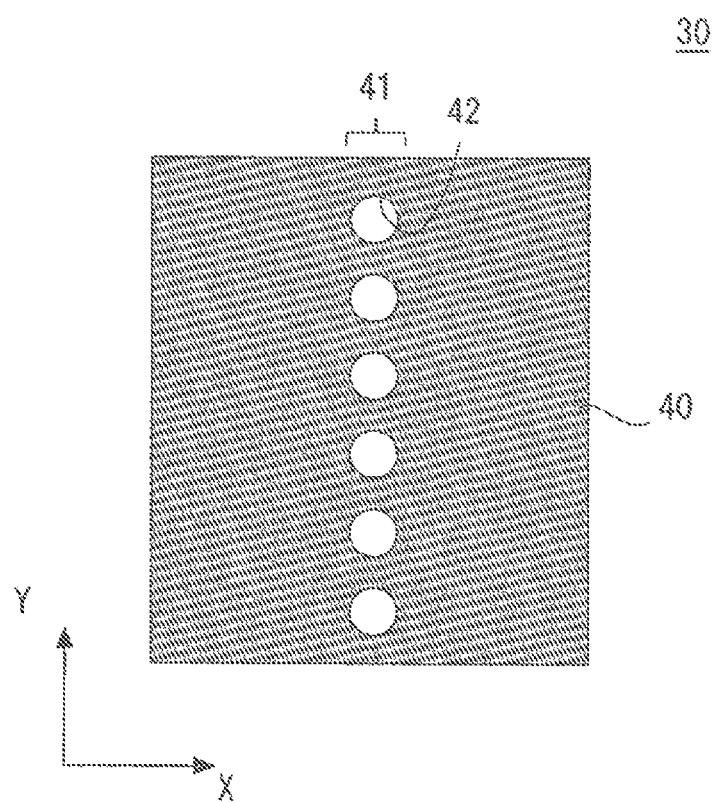
FIG. 2 shows a pinhole array disposed on the incoming side of a spectroscope.

As described above, the pinhole array 30 is arranged on the incoming side of the spectroscope 31. The pinholes of the pinhole array 30 define a measurement area(s) on the sample. A configuration of the pinhole array 30 is explained hereinafter with reference to FIG. 2. FIG. 2 is an XY-plane view showing a configuration of the pinhole array 30. The pinhole array 30 includes a light-shielding plate 40 in which a plurality of pinholes 42 are formed. For example, the pinholes 42 are formed by forming through-holes or a transparent pattern or the like in the light-shielding plate 40. In this example, six pinholes 42 are arranged in a row. Further, the pinholes 42 arranged in the Y-direction are arranged at regular intervals. Only the outgoing light that has entered the pinholes 42 pass through the light-shielding plate toward the detector 32 side. The outgoing light that is incident on the areas between the pinholes 42 is blocked by the light-shielding plate 40. The pinholes 42 serve as light-passage sections that allow the outgoing light to pass therethrough, and the areas other than the pinholes 42 serve as the light-shielding sections.

As described above, the arrangement direction of the pinholes 42 corresponds to the scanning direction of the Y-scanning unit 13. The light beam is scanned (i.e., moved) in the Y-direction by the Y-scanning unit 13. As a result, the spot of the outgoing light moves in the arrangement direction of the pinholes 42 on the pinhole array 30. Hereinafter, the area in which the pinholes 42. are arranged is referred to as "array section 41". The width of the entrance slit of an ordinary spectroscope corresponds to the width of the array section 41. Therefore, the wavelength resolution of the spectroscope 31 depends on the width of the array section 41. Note that the pinholes 42, which serve as the light-passage sections, are not limited to the configuration in which holes are physically formed. That is, a configuration in which light-passage sections are formed solely by transparent material may be also employed.

Figure 3A:
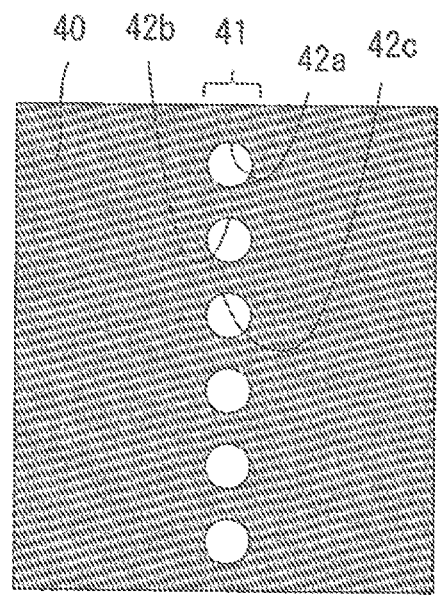
FIG. 3A is a diagram for explaining a relation between pinholes of a pinhole array and light spots on a light-receiving surface.
Figure 3A:
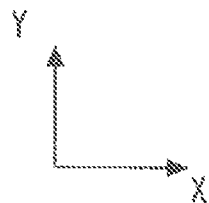
Figure 3B:
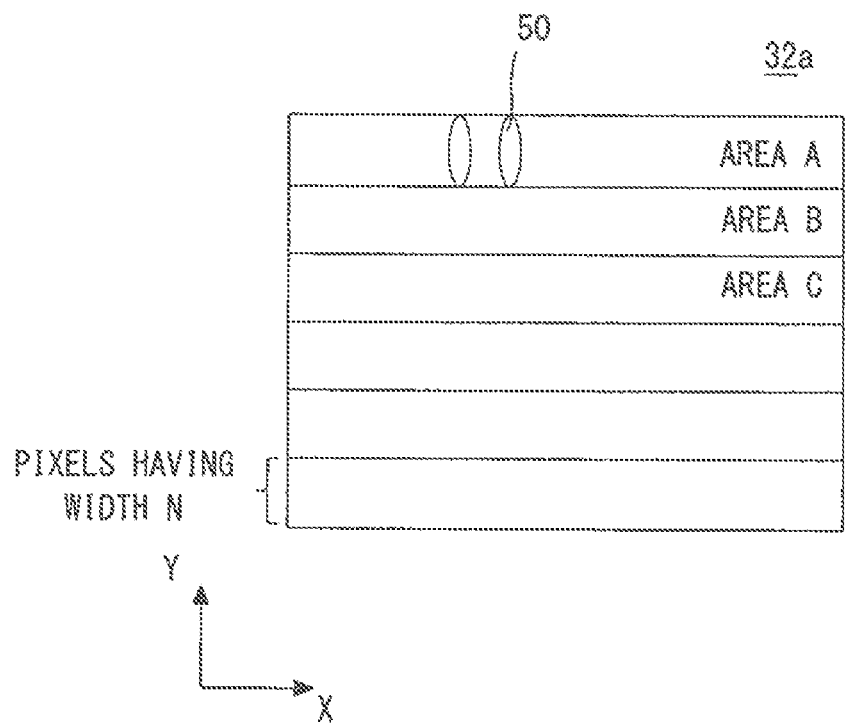
FIG. 3B is a diagram for explaining a relation between pinholes of a pinhole array and light spots on a light-receiving surface.

Next, a relation between the pinhole array 30 and the light-receiving surface of the detector 32 is explained with reference to FIGS. 3A and 3B. FIG. 3A shows the pinhole array 30, and FIG. 3B schematically shows the light-receiving surface 32a of the detector 32. Further, in FIG. 3A, in order to distinguish the pinholes of the pinhole array 30 from one another, the uppermost pinhole is referred to as "pinhole 42a"; the second pinhole is referred to as "pinhole 42b"; and the third pinhole is referred to as "pinhole 42c".

The outgoing light that has passed through the pinhole 42a is incident on an area A of the light-receiving surface 32a. The area A is a band-like area whose longitudinal direction coincides with the X-direction and in which the width direction of N pixels coincides with the Y-direction. Note that the outgoing light that has passed through the pinhole 42a is dispersed in the X-direction (wavelength direction) by the spectroscope 31. Therefore, the position in the X-direction on the detector 32 changes according to the wavelength of the outgoing light, which is the Raman-scattered light. Similarly, the outgoing light that has passed through the pinhole 42b is incident on an area B of the light-receiving surface 32a, and the outgoing light that has passed through the pinhole 42c is incident on an area C of the light-receiving surface 32a. Similarly to the area A, each of the areas B and C is a band-like area extending in the X-direction and in which the width direction of N pixels coincides with the Y-direction. The areas A, B and C are arranged so that they do not overlap each other. In this example, the areas A and B are arranged so as to be adjacent to each other. Similarly, the areas C and B are arranged so as to be adjacent to each other. Needless to say, each of the other outgoing light beams that have passed through the remaining pinholes 42 is also incident on a different band-like area in a similar manner.

When there is astigmatism or the like in the lens 24, the outgoing light spreads in the Y-direction and reaches the light-receiving surface 32a in the spread state. That is, the spot 50 on the light-receiving surface 32a spreads in the Y-direction. However, the area A has a certain width (N pixels in this example). Therefore, the outgoing light that has passed through the pinhole 42a never spreads beyond the area A on the light-receiving surface 32a. In other words, the outgoing light that has passed through the pinhole 42a is never incident on the adjacent area B. When the outgoing light that has passed through the pinhole 42a is to be detected, the signals of the pixels having the width N contained in the area A are added up and read. As a result, the Raman spectrum of the outgoing light that has passed through the pinhole 42a can be obtained.

Similarly, the outgoing light that has passed through the pinhole 42b never spreads beyond the area B on the light-receiving surface 32a. That is, the outgoing light that has passed through the pinhole 42b is incident on neither the area A nor the area C on the light-receiving surface 32a. Therefore, the outgoing light that has passed through the pinhole 42b is detected, on the light-receiving surface 32a, separately from the outgoing light beams that have passed through the other pinholes. This is also true for the other pinholes. Therefore, the outgoing light beams that come through adjacent pinholes 42 are incident on different band-line areas.

Note that the intervals between the pinholes 42 are determined so that the band-like areas do not overlap each other. That is, the intervals between the pinholes may be determined according to the magnitude of the astigmatism and/or the size of the pinholes. With the above-shown configuration, it is possible to prevent the outgoing light beams coming through adjacent pinholes 42 from overlapping each other on the light-receiving surface.

In this exemplary embodiment, a line-like area on the sample 22 is illuminated by scanning (i.e., moving) the laser light in the Y-direction at high speed. Further, a plurality of measurement areas located in the line-like area are measured at a time by one exposure. Further, in this exemplary embodiment, another scanning unit different from the Y-scanning unit 13 moves the laser light spot and the sample 22 relatively with respect to each other in the Y-direction. For example, the stage 23 may be used as another scanning unit.

Figure 4A:
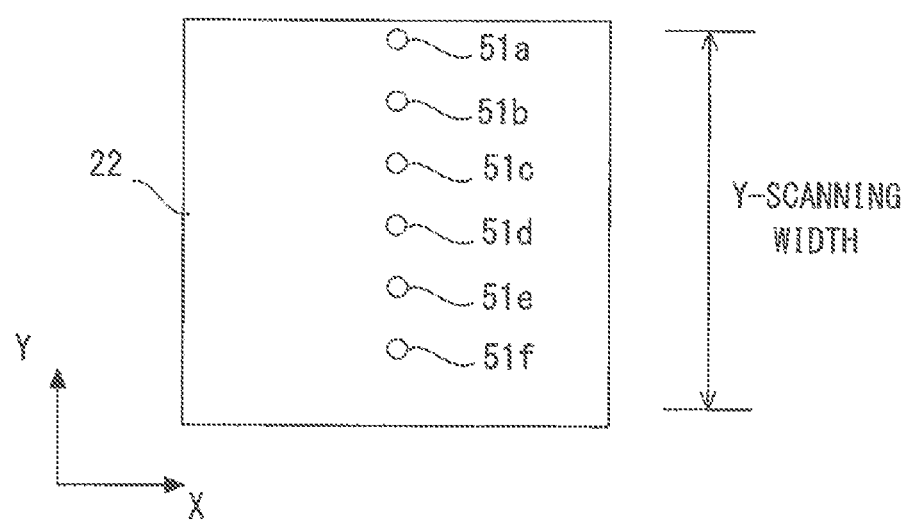
FIG. 4A is a plane view showing measurement areas on a sample by pinholes of a pinhole array.
Figure 4B:
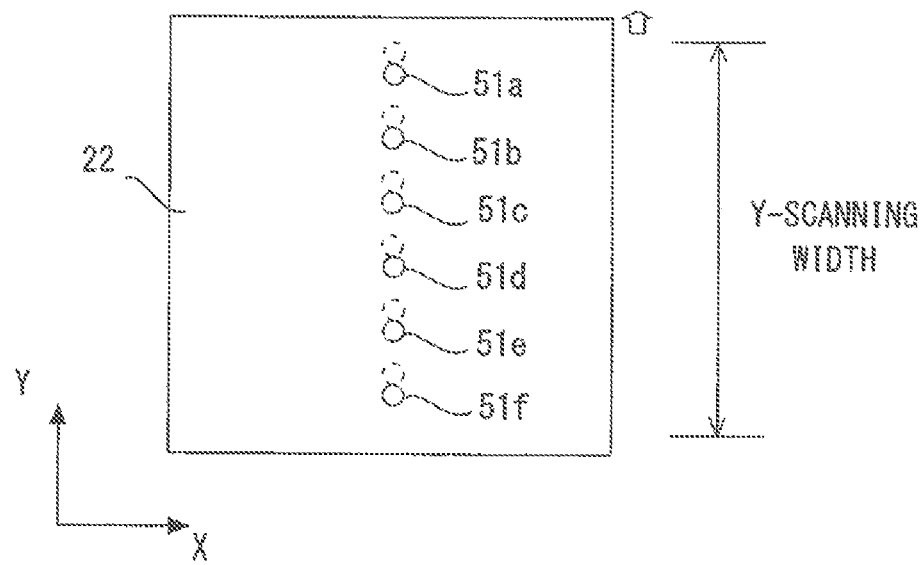
FIG. 4B is a plane view showing measurement areas on a sample by pinholes of a pinhole array.
Figure 4C:
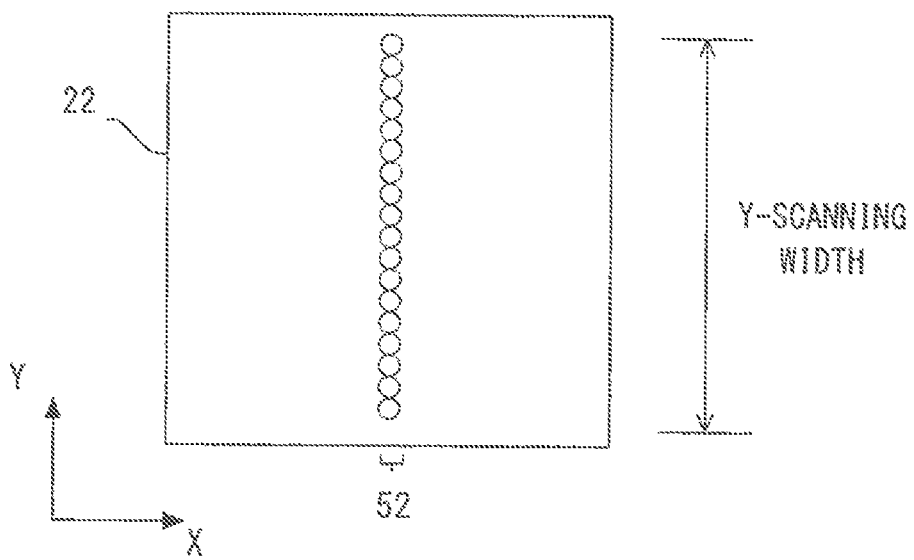
FIG. 4C is a plane view showing measurement areas on a sample by pinholes of a pinhole array.

Note that FIG. 4 shows a movement of the light spot(s) on the sample 22. FIG. 4A shows measurement areas that are measured by one measurement process. FIG. 4B shows measurement areas that are measured by the next one measurement process. FIG. 4C collectively shows measurement areas that are measured by a plurality of measurement processes. Note that the measurement area is an area of the sample 22 projected onto a pinhole 42 of the pinhole array 30. Therefore, the outgoing light emitted from the measurement area passes through the pinhole 42, and is divided into a spectrum and measured.

When Y-scanning is performed by the Y-scanning unit 13 with the scanning width shown in FIG. 4A, measurement areas 51a to 51f can he measured. The measurement areas 51a to 51f are interspersed along the Y-direction. That is, the measurement areas 51a to 51f are arranged at regular intervals. The measurement areas 51a to 51f are the areas corresponding to the pinholes 42. Specifically, Raman-scattered light generated in the measurement area 51a passes through the pinhole 42a shown in FIG. 3A, Similarly, Raman-scattered light generated in the measurement area 51b passes through the pinhole 42h. Therefore, when Y-scanning corresponding to one line is performed, only the interspersed measurement areas 51a to 51f can be measured. In other words, in the scanning performed by the Y-scanning unit 13, the outgoing light coming from any places other than the measurement areas 51a to 51f cannot pass through the pinholes 42. Even when scanning is performed by the Y-scanning unit 13, the outgoing light coming from any places between the measurement areas 51a to 51f is incident on the areas between the pinholes 42 and thereby blocked by the light-shielding plate 40.

Therefore, the stage 23 moves the sample 22 relatively with respect to the laser light spot in the Y-direction. In FIG. 4A, when the stage 23 moves the sample 22 in the direction indicated by the arrow (+Y direction) by a distance equivalent to one measurement area, the measurement areas 51a to 51f move relatively to the positions shown in FIG. 4B. Note that in FIG. 4B, circles drawn by dotted lines indicate measurement areas shown in FIG. 4A. In this way, by shifting the measurement areas 51a to 51f by a distance equivalent to one measurement area, different places on the sample 22 can be measured. That is, by illuminating the sample in the illumination state shown in FIG. 4B, places that are not measured in the illumination state shown in FIG. 4A can be measured. By driving the stage 23, different places can be measured, In this manner, the positions of the light spots on the sample 22 are changed by using another scanning unit different from the Y-scanning unit 13. Further, the spots are shifted by a distance equivalent to one measurement area at a time. By doing so, as shown in FIG. 4C, a line area 52 can be measured. Specifically, the Y-scanning unit 13 performs Y-scanning corresponding to one line and thereby measures the one line. After that, the measurement areas on the sample 22 are shifted by a distance equivalent to one measurement area in the Y-direction by using another scanning unit. By repeating these operations, it is possible to measure a set of measurement areas 51 consisting of a plurality of measurement areas and thereby to measure the entire line area 52. That is, by performing measurement of spot-like measurement areas 51 a plurality of times, it is possible to perform measurement corresponding to one line. Needless to say, the Y-scanning by using the stage does not necessarily have to be performed for one measurement area at a time.

Then, when the measurement of the line area 52 has been completed, the X-scanning mirror 18 performs X-scanning. In this example, the laser light spots are shifted by a distance equivalent to the one line width. The X-scanning mirror 18 is disposed on the optical path extending from the sample 22 to the beam splitter 17. Therefore, the outgoing light is descanned. Even if the laser light spots are shifted on the sample 22 by the scanning performed by the X-scanning mirror 18, the spot positions at the pinhole array 30 do not change. That is, the outgoing light is incident on the array section 41 of the pinhole array 30 regardless of the scanning position by the X-scanning mirror 18. Therefore, it is possible to illuminate the next line by the scanning performed by the X-scanning mirror 18. Needless to say, the X-scanning may be performed by using the stage 23 instead of using the X-scanning mirror 18.

Although the measurement areas are shifted in the Y-direction by using the stage 23 in the above explanation, the measurement areas may be shifted by using another scanner. For example, another Y-scanning unit different from the Y-scanning unit 13 may be disposed between the beam splitter 17 and the X-scanning mirror 18. This configuration will he explained later as a second exemplary embodiment. Further, when the intervals between measurement areas on the sample 22 (in the case of FIG. 4A, the intervals between the measurement areas 51a to 51f) are sufficiently small for the measurement purpose, the scanning performed by the scanning means other than the Y-scanning unit 13 is unnecessary.

Figure 5:
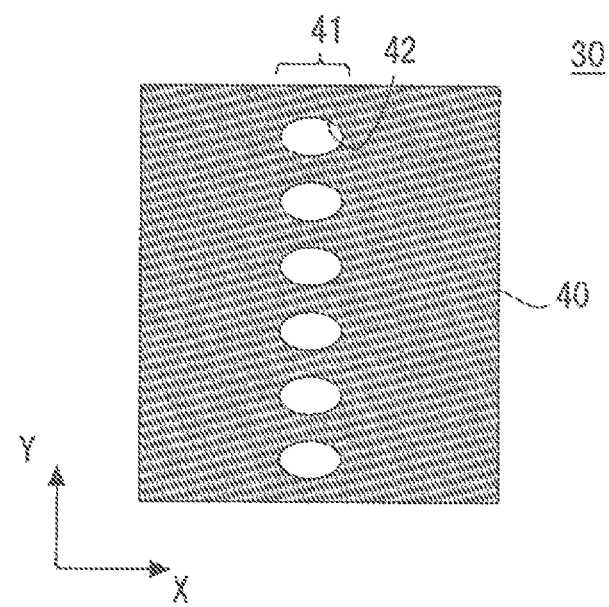
FIG. 5 is a plane view showing a pinhole array in which the size of pinholes is changed.

Next, a configuration in which the size of the pinholes 42 of the pinhole array 30 can be changed is explained. For example, when the outgoing light emitted from the sample 22 is weak, the size of the pinholes 42 is increased. By doing so, the amount of light detected in the detector 32 can be increased. Note that the pinholes 42 are widened in the direction perpendicular to the width direction of the array section 41, i.e., in the X-direction. That is, as shown in FIG. 5, the pinholes 42 are formed, for example, as elliptic holes whose longitudinal direction coincides with the X-direction. As a result, it is possible to prevent neighboring outgoing light beams that have passed through the pinholes 42 from overlapping each other and/or connecting with each other on the light-receiving surface 32a.

Configurations for adjusting the size of the pinholes 42 are explained with reference to FIGS. 6A to 8. Each of FIGS. 6A to 8 is a plane view showing a configuration for adjusting the size of the pinholes 42. Firstly, in a first configuration shown in FIGS. 6A and 6B, the pinhole array 30 is formed from a first plate 45 and a second plate 46. Note that the first plate 45 is a comb-teeth-like light-shielding plate and includes a transparent pattern 48 along the X-direction. The transparent pattern 48 includes rectangles whose longitudinal direction coincides with the X-direction. The number of transparent rectangles of the transparent pattern 48 corresponds to the number of pinholes 42 of the pinhole array 30. The second plate 46 is a rectangular-shaped light-shielding plate. The first and second plates 45 and 46 have roughly the same external size.

Figure 6A:
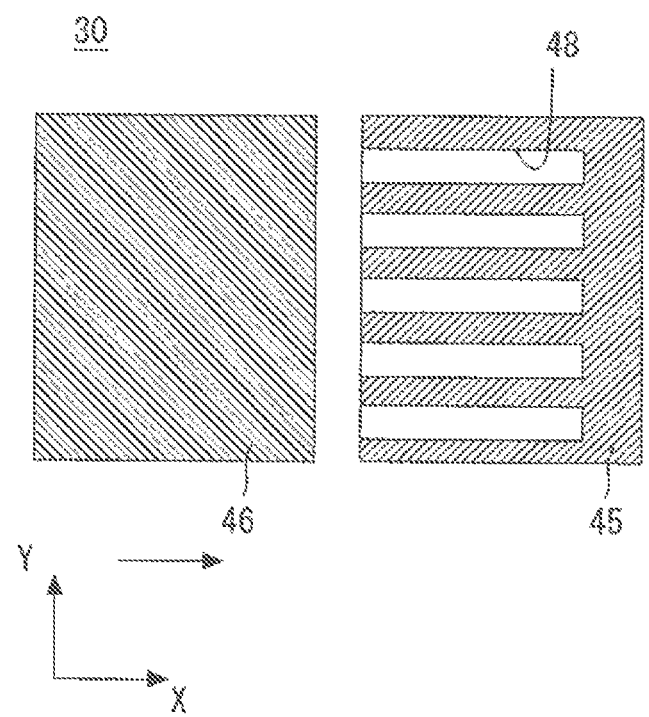
FIG. 6A is a plane view showing a first configuration in which the size of pinholes can be changed.
Figure 6B:
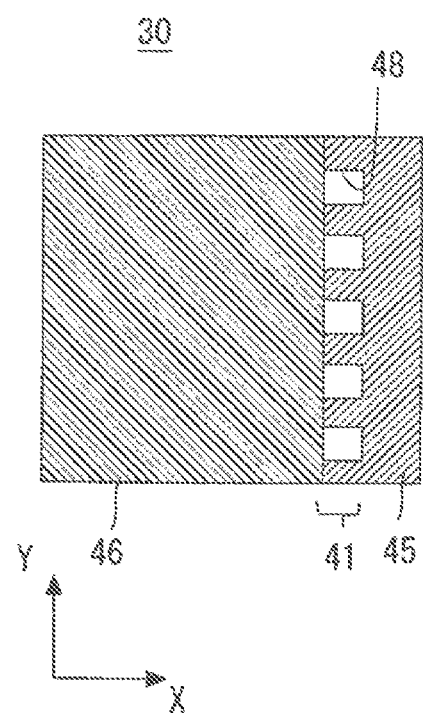
FIG. 6B is a plane view showing a first configuration in which the size of pinholes can be changed.

Further, the second plate 46 is moved in the direction indicated by the arrow from the state shown in FIG. 6A. As a result, as shown in FIG. 6B, the first and second plates 45 and 46 overlap each other. Consequently, a part of the transparent pattern 48 is shielded by the second plate 46. Therefore, the array section 41 is formed by the part of the transparent pattern 48 that is not covered by the second plate 46. Further, the width of the array section 41 can be changed by changing the relative positions of the first and second plates 45 and 46 in the X-direction. That is, the size of the part of the transparent pattern 48 that is covered by the second plate 46 is changed by moving one or both of the first and second plates 45 and 46. It is preferable that both of the first and second plates 45 and 46 are moved so that the centers of the openings do not move. By changing the size of the part of the transparent pattern 48 covered by the second plate 46, the width of the array section 41 can he changed. Therefore, it is possible to change the spot size of the outgoing light that enters the spectroscope 31. Therefore, it is possible to obtain sufficient amount of light for the measurement.

Figure 7B:
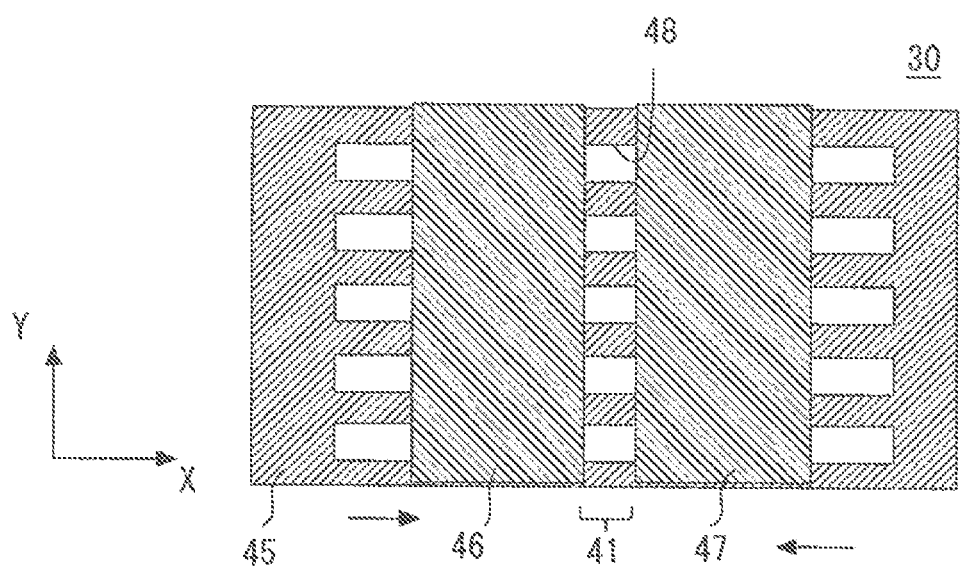
FIG. 7B is a plane view showing a second configuration in which the size of pinholes can be changed.

A second configuration for adjusting the size of the pinholes 42 is shown in FIGS. 7A and 7B. In FIGS. 7A and 7B, the pinhole array 30 is formed from a first plate 45, a second plate 46, and a third plate 47. The first plate 45 is a light-shielding plate including a stripe-like transparent pattern 48. The transparent pattern 48 has a rectangular shape whose longitudinal direction coincides with the X-direction. Each of the second and third plates 46 and 47 is a rectangular-shaped light-shielding plate. Further, as shown in FIG. 7A, the second and third plates 46 and 47 are disposed on both sides of the first plate 45. Each of the second and third plates 46 and 47 functions as variable-width slits. By moving the second and third plates 46 and 47 closer to each other, a configuration shown in FIG. 7 is obtained. The size of the part of the transparent pattern 48 that is covered by the second and third plates 46 and 47 is changed according to the distance between the second and third plates 46 and 47. Therefore, it is possible to change the width of the array section 41 and thereby to change the spot size of the outgoing light that enters the spectroscope 31. Therefore, it is possible to obtain sufficient amount of light for the measurement. Note that in the second configuration, similarly to the first configuration shown in FIGS. 6A and 6B, a first plate 45 composed of a comb-teeth-shaped light-shielding plate may be used.

Figure 8:
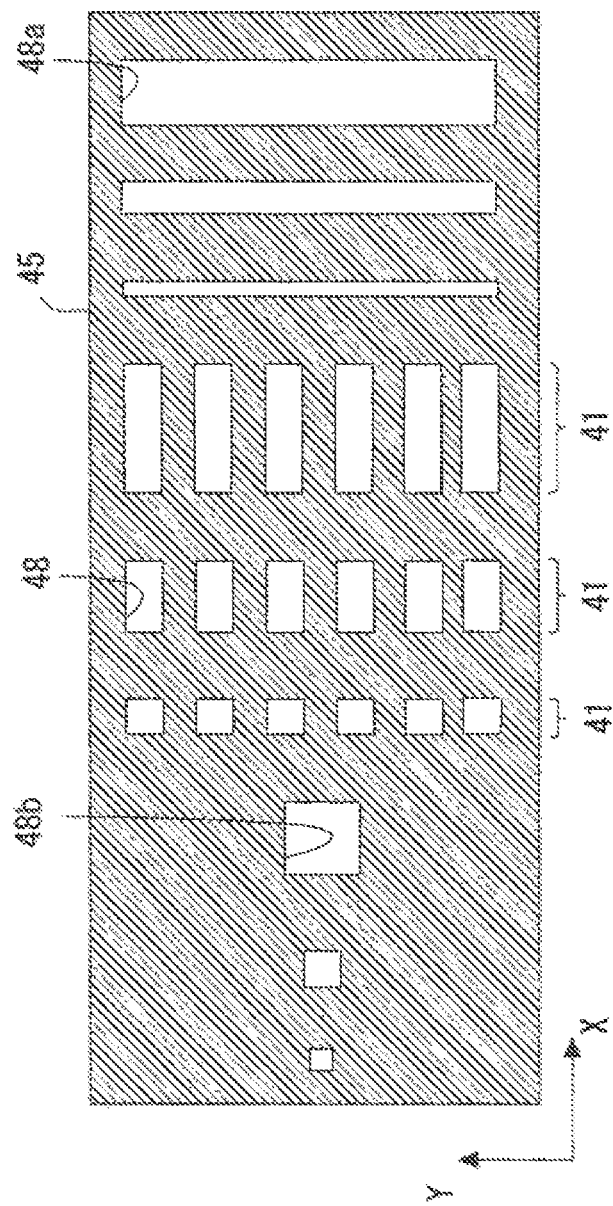
FIG. 8 is a plane view showing a third configuration in which the size of pinholes can be changed.

In a third configuration shown in FIG. 8, transparent patterns 48 having various sizes of transparent sections are formed. A number of transparent patterns 48 having different sizes of transparent sections are formed, In order to form the array section 41, transparent sections having the same size are arranged in a row in the Y-direction in each transparent pattern 48. Further, transparent patterns 48a each formed as a slit whose longitudinal directions coincide with the Y-direction are also prepared. Further, transparent patterns 48b each including only one pinhole are also prepared. In addition, each of the transparent patterns 48, 48a and 48b include three types of patterns having different widths.

As described above, the transparent patterns 48, 48a and 48b having different widths in the X-direction are formed in one first plate 45. By moving the first plate 45 in the X-direction, the width of the slit or the pinhole can be changed in a stepwise manner. The spot size of the outgoing light that enters the spectroscope 31 can be changed. As a result, it is possible to obtain sufficient amount of light for the measurement. Further, in the third configuration, in the case where the Y-scanning unit 13 is stopped and a single point on the sample 22 is measured, it is possible to improve the spatial resolution by using a transparent pattern 48 including only one pinhole. It is possible to reduce the measurement time by using a transparent pattern 48 formed as a slit. Further, it is also possible to perform measurement while switching the transparent pattern among the single pinholes, the slits, and the pinhole arrays.

Further, it is also possible to arrange transparent patterns 48 having different widths in the Y-direction and thereby to change the width by moving the first plate 45 in the Y-direction. With this configuration, although the movement amount of the first plate for changing the width increases, it is possible to prevent the position of the openings) from being shifted in the X-direction due to the switching and thereby to prevent the errors in measured wavelengths that would be otherwise caused by the switching.

In the above-described first to third configurations, it is possible to change the size of the pinholes 42 in the X-direction while maintaining the constant size hi the Y-direction. Note that the first plate 45 shown in the first to third configurations may be manufactured by using, for example, a lithography technique. Specifically, a chromium light-shielding film or the like is formed on a transparent substrate such as a glass substrate. Then, patterning is performed on the light-shielding film by using a lithography technique. As a result, a pattern having a predetermined shape can be formed. Alternatively, the first plate 45 can be manufactured by performing laser processing, etching processing, electroforming processing, or the like on a thin metal sheet.

In this exemplary embodiment, a confocal optical system using a pinhole array 30, instead of the slit, is employed. As a result, it is possible to improve the spatial resolution. It is preferable that a plurality of pinholes 42 are formed so that outgoing light beams that have passed through the pinholes 42 do not overlap each other on the light-receiving surface 32a of the detector 32. Specifically, the width of a plurality of pinholes is determined so that signals coming through the pinholes do not overlap each other. In reality, a signal coming through a pinhole does not have a finite size. Therefore, the width is preferably determined so that at least 90% of the signal coming through one pinhole, for example, is included within the pixels having the width N.

As a result, even when there is astigmatism in the optical system of the spectroscope 31 and thus the outgoing light that has passed through the pinholes 42 spreads, it is still possible to perform measurement with a high resolution. That is, it is possible to reduce the effect of the astigmatism of the optical system of the spectroscope 31 and thereby to improve the resolution. Since outgoing light beams corning through a plurality of spots can be measured at a time, the measurement time can be reduced. Further, the pinhole array 30 may be configured so that the size of the pinholes of the pinhole array 30 can be adjusted. As a result, it is possible to obtain sufficient amount of light for the measurement. Further, the size of the pinholes 42 may be determined according to the necessary resolution and the necessary amount of light for the measurement. Further, another Y-scanning means may be disposed in addition to the Y-scanning unit 13, which is disposed closer to the laser light source 10 than the X-scanning mirror 18 is. As a result, it is possible to measure the entire line area 52.

Further, by using the pinhole array 30 in which the pinholes 42 are arranged in a row the passage of the light can be restricted with a simple configuration. For example, in the case of a configuration in which a lattice-pattern pinhole array and a fiber bundle are used as in the case of Non-patent literature 2, it is necessary to rearrange the lattice-pattern fiber bundle into a line-like arrangement. In the configuration using the pinhole array 30, the task for rearranging the fiber bundle and the like can be omitted. The pinhole array 30 is disposed on the optical path extending from the beam splitter 17 to the spectroscope 31. That is, the light emitted from the laser light source 10 is not directly incident on the pinhole array 30, but the Raman-scattered light separated by the beam splitter 17 is incident on the pinhole array 30. With this configuration, it is possible to prevent the scattered illumination light from entering the spectroscope 31 through the pinhole array 30.

Further, as shown in Patent literature 1, the light may be spread in the Y-direction by using a cylindrical lens or the like, and then the spread light may be scanned (i.e., moved) by the Y-scanning unit 13. Alternatively, as shown in Japanese Unexamined Patent Application Publication No. 2006-

258990, the light may be spread in the Y-direction by using a cylindrical lens, and then a line-like area on the sample 23 may be illuminated by the spread light. For example, a line-like focus is formed on the surface of the diaphragm 15 by using one cylindrical lens. Then, the line-like light is projected on the sample 22. By disposing the means for converting light into line-like light as described above, it is possible to eliminate the need for the Y-scanning unit 13. In comparison to the multi-focus illumination configuration using a micro-lens array as shown in Non-patent literature 2, the line illumination configuration using the Y-scanning unit 13 or the cylindrical lens makes the adjustment easier.

Second Exemplary Embodiment

Figure 9:
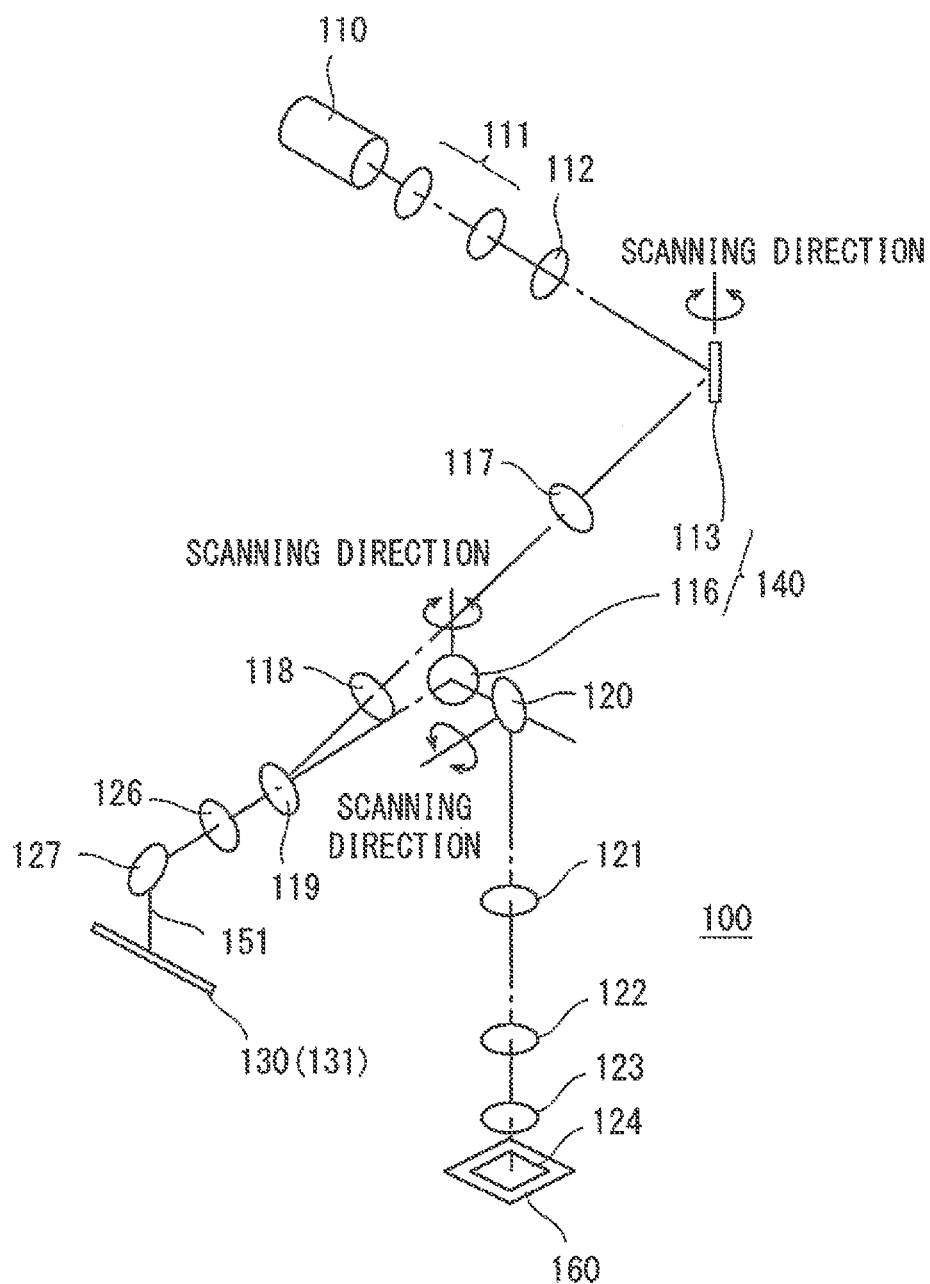
FIG. 9 shows a configuration of an optical microscope according to a second exemplary embodiment of the present invention.

An optical microscope and a spectrometry method according to this exemplary embodiment are explained with reference to FIG. 9. In this exemplary embodiment, instead of the Y-scanning performed by the stage 23 shown in the first exemplary embodiment, a Y-scanning mirror such as a galvano mirror is used. In this exemplary embodiment, a Y-scanning mirror is disposed in the vicinity of the X-scanning mirror.

An optical microscope according to an exemplary embodiment of the present invention is explained with reference to FIG. 9. FIG. 9 schematically shows a configuration of an optical system of an optical microscope 100 according to this exemplary embodiment. The optical microscope 100 includes, as a configuration for observing a sample 124, a laser light source 110, a beam expander 111, a laser line filter 112, a Y-scanning unit 140, a relay lens 114, a relay lens 115, a relay lens 117, a relay lens 118, an edge filter 119, an X-scanning unit 120, a relay lens 121, a tube lens 122, an objective lens 123, an imaging lens 126, a mirror 127, a spectroscope 131, and a stage 160. The Y-scanning unit 140 includes a high-speed scanner 113 and a low-speed scanner 116. Each of the high-speed scanner 113 and the low-speed scanner 116 is a scanning mirror such as a galvano mirror, and deflects a light beam.

The laser light source 110, the beam expander 111, the high-speed scanner 113, the relay lens 117, the relay lens 118, the edge filter 119, the X-scanning unit 120, the relay lens 121, the tube lens 122, the objective lens 121 the stage 160, and the imaging lens 126 are similar to the laser light source 10, the beam expander 11, the lens 14, the lens 16, the beam splitter 17, the X-scanning mirror 18, the lens 19, the lens 20, the objective lens 21, the stage 23, and the lens 24, respectively, shown in the first exemplary embodiment, and therefore their explanation is omitted. Further, other fundamental configurations are also similar to those shown in FIG. 5 of Japanese Unexamined Patent Application Publication No. 2010-54368, and therefore their explanation is omitted.

In this exemplary embodiment, the spectroscope 131 includes a pinhole array 130. The pinhole array 130 is similar to the pinhole array 30 shown in the first exemplary embodiment. The high-speed scanner 113 illuminates a line area in a similar manner to the Y-scanning unit 13 of the first exemplary embodiment, In this exemplary embodiment, the low-speed scanner 116 is additionally disposed between the X-scanning unit 120 and the edge filter 119. The low-speed scanner 116 performs Y-scanning on behalf of the stage 23 shown in the first exemplary embodiment. As a result, the laser light and its outgoing light are scanned in the Y-direction. The low-speed scanner 116 descans the outgoing light. As a result, the entire line area can be illuminated. Therefore, advantageous effects similar to those of the first exemplary embodiment can be obtained.

Third Exemplary Embodiment

In the first and second exemplary embodiments, a spot(s) is scanned (i.e., moved) by the scanning performed by the Y-scanning unit 13 or the high-speed scanner 113. In this process, evenly-spaced points in a line area are measured. That is, the areas between the measurement areas are not measured, though they are illuminated, unless scanning is performed by the stage 23 or the low-speed scanner 116. Therefore, the major part of the illumination light may not be effectively used. Further, a larger amount of light needs to be applied to the sample in order to obtain data having the same quality. Therefore, depending on the light illumination, the sample suffers increased damage.

Figure 10:
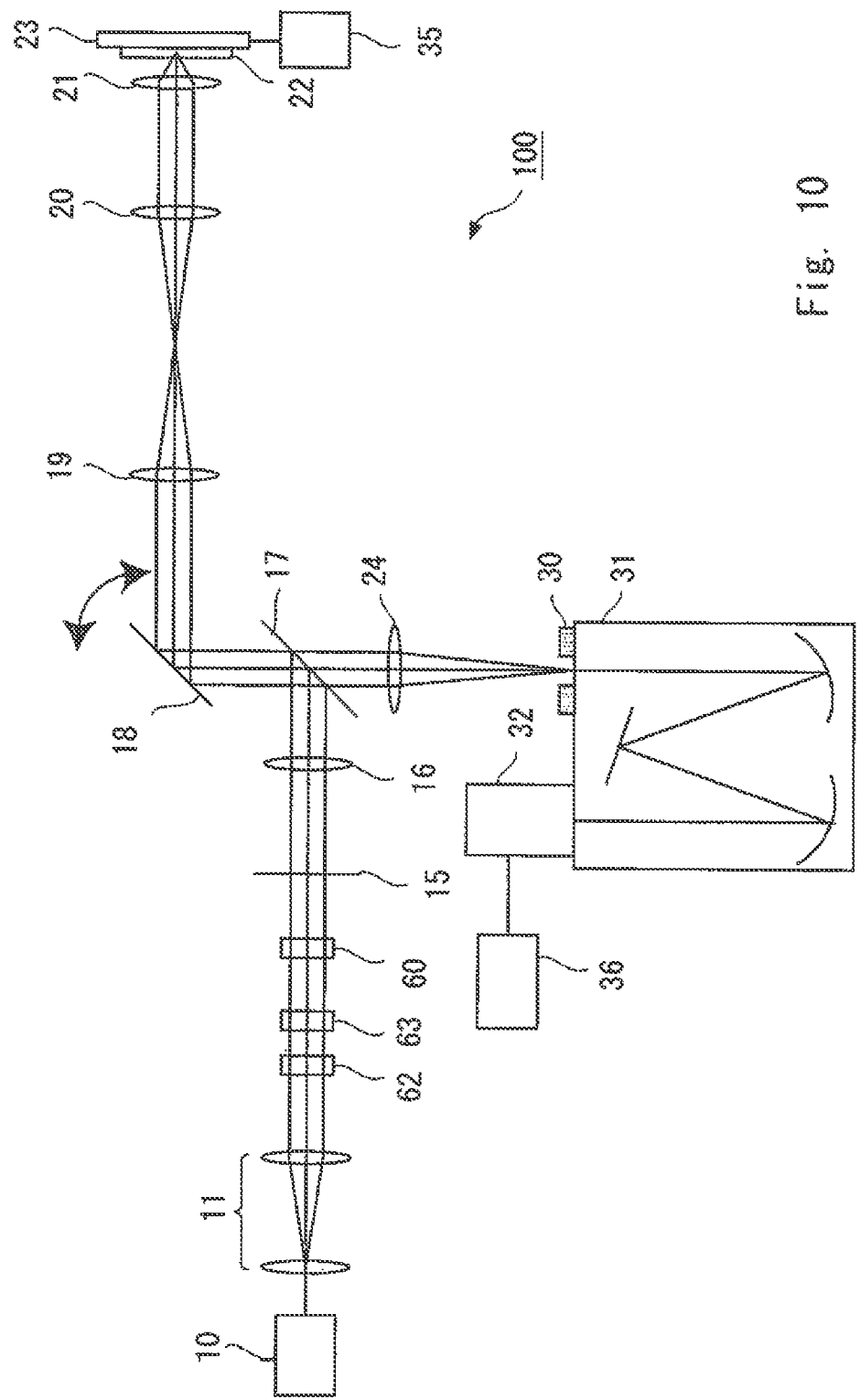
FIG. 10 shows a configuration of an optical microscope according to a third exemplary embodiment of the present invention.
Figure 11:
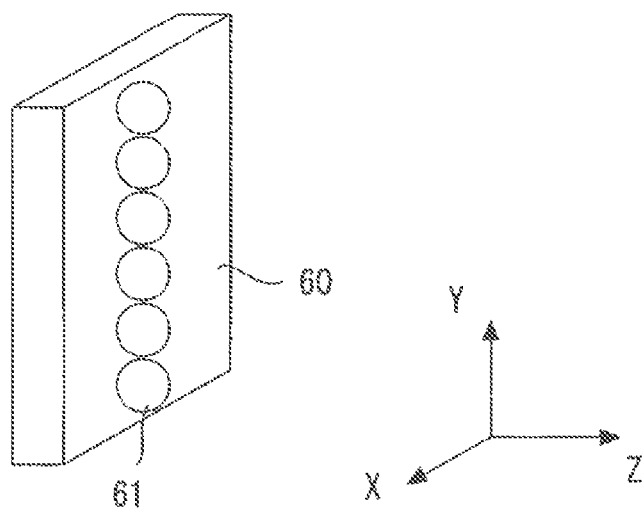
FIG. 11 is a perspective view showing a configuration of a micro-lens array.
Figure 12:
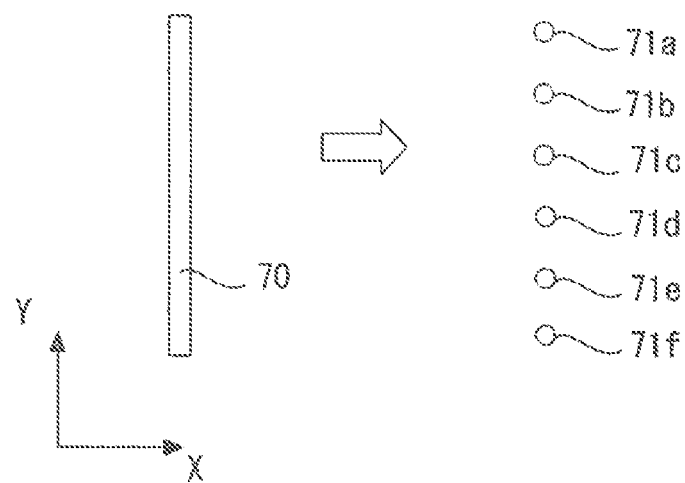
FIG. 12 shows an aspect in which a plurality of spots are formed by a micro-lens array.
Figure 13:
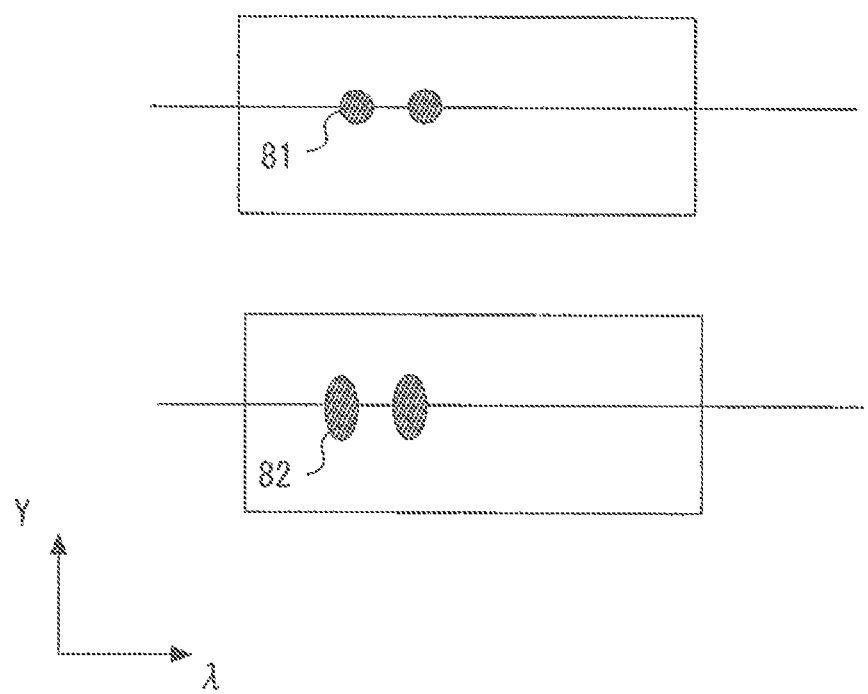
FIG. 13 shows an aspect in which a spot(s) is elongated on the light-receiving surface of a detector due to astigmatism.

Therefore, the illumination system is modified in this exemplary embodiment. Specifically, multi-beams are formed by using a micro lens array. This configuration is explained with reference to FIGS. 10 to 12. In FIG. 10, cylindrical lenses 62 and 63 and a micro-lens array 60 are used in place of the Y-scanning unit 13 and the lens 14 used in the configuration shown in FIG. 1. FIG. 11 is a perspective view showing a configuration of the micro-lens array 60. FIG. 12 shows an aspect in which a plurality of spot illuminations are formed by the micro-lens array 60. Note that the fundamental configuration of the optical microscope 100 is similar to that in the first exemplary embodiment, and therefore its explanation is omitted.

The cylindrical lenses 62 and 63 convert the laser light into line-like collimated light. The pair of cylindrical lenses 62 and 63 form line-like collimated light 70 that spreads in the direction perpendicular to the surface of the drawing, i.e., in the Y-direction (see FIG. 12). The line-like collimated light 78 propagates in parallel with the optical axis and enters the micro-lens array 60. As shown in FIG. 11, the micro-lens array 60 includes a plurality of lenses 61 arranged in the Y-direction. Each lens 61 of the micro-lens array 60 concentrates the incoming laser light. The plurality of lenses 61 of the micro-lens array 60 form a plurality of spot illuminations $71a$ to $71f$ in the place where the diaphragm 15 is placed (see FIG. 12). As a result, multi-beams for forming a plurality of spots can be generated. These spot illuminations $71a$ to $71f$ are projected on the sample 22 through the lens 16, the lens 19, the lens 20, and the objective lens 21. Therefore, a plurality of spots on the sample 22 can be simultaneously illuminated.

Further, the intervals between the spot illuminations on the sample 22 are conformed to the intervals between the measurement areas $51a$ to $51f$ formed by the pinhole array 30. As a result, outgoing light emitted from the places at which the laser light is incident passes through the pinholes 42 of the pinhole array 30. For example, when the spot illuminations formed by the micro-lens array 60 are incident on the sample 22, outgoing light emitted from the area of the sample 22 onto which the illumination light $71a$ is projected enters the pinhole $42a$. The other outgoing light beams generated by the other spots $71b$ to $71f$ also pass through their respective pinholes 42. Therefore, it is possible to simultaneously illuminate the plurality of measurement areas $51a$ to $51f$ formed by the pinhole array 30.

The plurality of illumination spots formed by the micro-lens array 60 are conformed to the measurement areas formed by the pinhole array 30. As a result, it is possible to effectively use the laser light. Further, since no light is applied to the parts that are not measured, the damage on the sample 22 can be reduced. Further, it is possible to use the light with efficiency. Further, similarly to the first exemplary embodiment, spot-like areas are illuminated. Then, the outgoing light emitted from the spot-like areas is detected through the pinhole array 30. Therefore, the measurement is performed through a confocal optical system. As a result, it is possible to improve the spatial resolution in the Y-direction grid in the Z-direction in comparison to the related-art configuration in which only the confocal effect by the slit is used.

Note that the line-like collimated light 70 may be formed by using an anamorphic prism(s) instead of using the cylindrical lenses 62 and 63. By using a pair of cylindrical lenses 62 and 63 or an anamorphic prism(s) as described above, the beam can be spread in the direction along which the lenses 61 are arranged. Further, a combination of a diffractive optical element(s) and a lens(es) may be used as elements for forming the plurality of spot illuminations arranged in a row. That is, there are no particular restrictions on the multi-beam forming means for forming a plurality of spots on the sample 22.

With the above-described optical microscope, it is possible to measure a Raman spectrum. Note that although the optical microscope 100 that performs spectrometry for Raman-scattered light is explained in above explanation, the present invention not limited to such optical microscopes. The present invention can be applied to any spectrometry device that detects outgoing light that is emitted from a sample with a laser wavelength different from that of the incoming light. For example, the present invention may be applied to a spectrometry device that detects fluorescence excited by exciting light and a spectrometry device that detects infrared absorption. In these spectrometry devices, a spectrum can be also measured in a short time.

This application is based upon and claims the benefit of priority from Japanese patent application No. 2011-54538, filed on Mar. 11, 2011, the disclosure of which is incorporated herein in its entirety by reference.

INDUSTRIAL APPLICABILITY

The present invention can be used for spectrometry in which light from a sample is divided into a spectrum and measured.

REFERENCE SIGNS LIST

10 LASER LIGHT SOURCE
11 BEAM EXPANDER
13 Y-SCANNING UNIT
14 LENS
15 DIAPHRAGM
16 LENS
17 BEAM SPLITTER
18 X-SCANNING MIRROR
19 LENS
20 LENS
21 OBJECTIVE LENS
22 SAMPLE
23 STAGE
24 LENS
25 DIAPHRAGM
26 LENS
27 FILTER
28 FILTER
29 FILTER DRIVING UNIT
30 PINHOLE ARRAY
31 SPECTROSCOPE
32 DETECTOR
32a LIGHT-RECEIVING SURFACE 32A
35 STAGE DRIVING UNIT
36 PROCESSING UNIT
40 LIGHT-SHIELDING PLATE
41 ARRAY SECTION
42 PINHOLE
45 FIRST PLATE
46 SECOND PLATE
47 THIRD PLATE
48 TRANSPARENT PATTERN
50 SPOT
51 SPOT
51a-51e SPOT
52 LINE AREA
60 MICRO-LENS ARRAY
61 LENS
70 LINE-LIKE COLLIMATED LIGHT
71a-71e SPOT
81 SPOT
82 SPOT
100 OPTICAL MICROSCOPE
110 LASER LIGHT SOURCE
111 BEAM EXPANDER
112 LASER LINE FILTER
113 HIGHSPEED SCANNER
114 RELAY LENS
115 RELAY LENS
116 LOW-SPEED SCANNER
117 RELAY LENS
118 RELAY LENS
119 EDGE FILTER
120 X-SCANNING UNIT
121 RELAY LENS
122 TUBE LENS
123 OBJECTIVE LENS
126 IMAGING LENS
127 MIRROR
131 SPECTROSCOPE
140 Y-SCANNING UNIT
160 STAGE

The invention claimed is:

1. An optical microscope comprising:
a light source;
an objective lens that concentrates a light beam from the light source and applies the concentrated light beam onto a sample;
scanning means for moving a position of the light beam relatively with respect to the sample and thereby scanning a spot position of the light beam on the sample;
light branching means for separating, among the light beam incident on the sample, outgoing light emitted from the sample toward the objective lens side from the light beam emitted from the light source and incident on the sample, the outgoing light being emitted with a different wavelength;
a spectroscope that spatially disperses the outgoing light separated by the light branch means according to a wavelength;
a 2D array photodetector that comprises light-receiving pixels arranged in an army and detects the outgoing light dispersed by the spectroscope; and
light restricting means disposed on an incoming side of the spectroscope, a plurality of light-passage sections being arranged along a direction perpendicular to a dispersing direction of the spectroscope in the light restricting means, the plurality of light-passage sections being adapted to allow concentrated outgoing light separated from the light beam by the light branching means to pass therethrough to the spectroscope side; and a lens that concentrates the outgoing light separated from the light beam by the light branching means onto the light restricting means; wherein the plurality of light-passage sections are formed so that the outgoing lights that has passed through the plurality of light-passage sections does not overlap each other on a light-receiving surface of the 2D array photodetector, wherein the outgoing light that has passed though one light passage section is incident on N, wherein N is an integer equal to or more than 2, pixels perpendicular to the dispersing direction of the 2D array photodetector, a processing apparatus comprising a processor; and a memory configured to store signal from the 2D array photodetector; and wherein signals of the N pixels are added up by the processing apparatus;

wherein the light restricting means includes at least one plate configured to form the plurality of light-passage sections, wherein the processing apparatus is configured to change a size of the light-passage sections in a direction in parallel with the dispersing direction by moving the plate, and wherein the size of the light-passage sections is fixed in a direction perpendicular to the dispersing direction.

2. The optical microscope according to claim 1, wherein the plurality of light-passage sections are formed so that outgoing light that has passed through the plurality of light-passage sections does not overlap each other on a light-receiving surface of the 2D array photodetector.

3. The optical microscope according to claim 1, wherein the plurality of light-passage sections are formed by a pinhole array, pinholes being arranged in a row in the pinhole array.

4. The optical microscope according to claim 1, further comprising multi-beam forming means for forming a plurality of light beam spots incident on the sample so that measurement areas by the plurality of light-passage sections are simultaneously illuminated.

5. The optical microscope according to claim 4, wherein the multi-beam forming means arranges the plurality of light beam spots in a row.

6. The optical microscope according to claim 1, wherein the scanning means comprises:

a first scanning unit that deflects the light beam from the light source in a first direction so that a position of the outgoing light in the light restricting means changes in an arrangement direction of the light-passage sections, the first scanning unit being disposed on an optical path extending from the light source to the light branching means, the first scanning unit including an optical scanner for changing an outgoing angle of the light beam; and a second scanning unit that scans the spot position of the light beam on the sample in a second direction different from the first direction, the second scanning unit being disposed on an optical path extending from the light branching means to the sample.

7. The optical microscope according to claim 6, wherein the scanning means further comprises a third scanning unit that moves the position of the light beam relatively with respect to the sample and thereby scans the spot position of the light beam on the sample, and measurement areas of the light-passage sections and the light beam spots are moved in the first direction on the sample by the scanning of the third scanning unit.

8. A spectrometry method comprising:

concentrating a light beam from a light source and applying the concentrated light beam onto a sample;

moving a position of the light beam relatively with respect to the sample and thereby scanning a spot position of the light beam on the sample;

separating, among the light beam incident on the sample, outgoing light emitted from the sample toward the objective lens side from the light beam emitted from the light source and incident on the sample, the outgoing light being emitted with a different wavelength;

concentrating the outgoing light separated from the light beam;

applying the concentrated outgoing light onto light restricting means, a plurality of light-passage sections being arranged in the light restricting means, the plurality of light-passage sections allowing the concentrated outgoing light separated from the light beam by the light branching means to pass therethrough;

dispersing the outgoing light that has passed through the light-passage sections, in a direction perpendicular to an arrangement direction of the light-passage sections according to a wavelength; and detecting, by a 2D array photodetector comprising light-receiving pixels arranged in an array, the dispersed outgoing light; and a lens that concentrates the outgoing light separated from the light beam by the light branching means onto the light restricting means; wherein the plurality of light-passage sections are formed so that the outgoing lights that has passed through the plurality of light-passage sections does not overlap each other on a light-receiving surface of the 2D array photodetector, wherein the outgoing light that has passed though one light passage section is incident on N, wherein N is an integer equal to or more than 2, pixels perpendicular to the dispersing direction of the 2D array photodetector, wherein signals of the N pixels are added up, wherein the light restricting means includes at least one plate configured to form the plurality of light-passage sections, wherein a size of the light-passage sections are changed in a direction in parallel with the dispersing direction by moving the plate, and wherein the size of the light-passage sections is fixed in a direction perpendicular to the dispersing direction.

9. The spectrometry method according to claim 8, wherein the plurality of light-passage sections are formed so that outgoing light that has passed through the plurality of light-passage sections does not overlap each other on a light-receiving surface of the 2D array photodetector.

10. The spectrometry method according to claim 8, wherein the plurality of light-passage sections are formed by a pinhole array, pinholes being arranged in a row in the pinhole array.

11. The spectrometry method according to claim 8, wherein a plurality of light beam spots incident on the sample are formed so that measurement areas by the plurality of light-passage sections are simultaneously illuminated.

12. The spectrometry method according to claim 11, wherein the plurality of light beam spots on the sample are arranged in a row.

13. The spectrometry method according to claim 8, wherein the spot position of the light beam on the sample is scanned in a first direction so that a line-shaped area on the sample is measured, and after the measurement for the line-shaped area, the spot position of the light beam on the sample is scanned in a second direction.

14. The spectrometry method according to claim 13, wherein when the spot position of the light beam on the sample is scanned in the first direction, the light beam from the light source is deflected in the first direction without descanning the light beam, and then the measurement area of the light-passage sections on the sample is moved in the first direction.

* * * * *